United States Patent [19]
Montner et al.

[11] Patent Number: 5,510,335
[45] Date of Patent: Apr. 23, 1996

[54] EXERCISE HYDRATION REGIMEN TO ENHANCE EXERCISE ENDURANCE AND PERFORMANCE

[75] Inventors: Paul Montner, Albuquerque, N.M.; Thomas W. Chick, Bay City, Tex.; Dan Stark; Marvin L. Riedesel, both of Albuquerque, N.M.

[73] Assignee: University of New Mexico, Albuquerque, N.M.

[21] Appl. No.: 369,757

[22] Filed: Jan. 6, 1995

Related U.S. Application Data

[63] Continuation of Ser. No. 55,003, Apr. 30, 1993, Pat. No. 5,403,921.
[51] Int. Cl.⁶ .................................................. A61K 31/70
[52] U.S. Cl. .......................... 514/23; 424/439; 424/722; 426/810; 514/460; 514/738; 536/1.11
[58] Field of Search ...................... 424/722, 439; 426/810; 536/1.11; 514/23, 460, 738

[56] References Cited

U.S. PATENT DOCUMENTS

| | | | |
|---|---|---|---|
| 3,894,148 | 7/1975 | Ecker | 424/439 |
| 4,981,687 | 1/1991 | Fregly et al. | 424/439 |
| 5,147,650 | 9/1992 | Fregly et al. | 424/439 |
| 5,236,712 | 8/1993 | Fregly et al. | 424/439 |
| 5,238,684 | 8/1993 | Fregly et al. | 424/439 |
| 5,403,921 | 4/1995 | Montner et al. | 424/722 |

*Primary Examiner*—Ronald W. Griffin
*Attorney, Agent, or Firm*—Hoffman, Wasson & Gitler

[57] ABSTRACT

An exercise regimen which enhances exercise endurance and performance. The regimen includes pre-exercise hydration with a glycerol solution combined with hydration during exercise with a glycerol based solution to prolong hydration effects. The first pre-exercise glycerol solution regimen begins 2 hours prior to exercise and ends ½ hour before exercise begins. The hydration during exercise regimen combines glycerol with a carbohydrate and sodium to prolong fluid retention.

3 Claims, No Drawings

EXERCISE HYDRATION REGIMEN TO ENHANCE EXERCISE ENDURANCE AND PERFORMANCE

GOVERNMENT RIGHTS

This invention was made in the performance of work supported by the National Institute of Health GCRC Award #5M0IRR00997-16 through the University of New Mexico Clinical Research Center, and the U.S. Government has certain rights therein.

This is a continuation of application Ser. No. 08/055,003 filed on Apr. 30, 1993, now U.S. Pat. No. 5,403,921.

BACKGROUND OF THE INVENTION

The present invention relates to an exercise regimen which enhances exercise endurance by hydration with a glycerol solution prior to inception of exercise, combined with hydration during exercise with a glycerol and carbohydrate based solution to optimize endurance.

Oral replacement solutions are widely used in athletic and recreational events. Strenuous exercise as well as exposure to sunlight and heat can cause significant physiological changes. Subjects exercising or working in the heat or for prolonged periods of time are at risk for developing impaired function or heat-related injuries. In order to prevent heat-related injuries such as heat exhaustion, heat stroke and dehydration syndrome, a number of compositions and solutions have been suggested.

In the Runner's World article, entitled "*HYPERHYDRATION*" by Liz Applegate (September 1992), glycerol has been suggested as a way to preserve blood volume, moderate heart rate and allow more blood to be sent to the skin for cooling. No analysis of a particular use or regimen is discussed nor are there specifics given concerning when to use it or in what combination or proportions thereof.

Further, in a published study by Koenigsberg et al, entitled, "40 *hour Glycerol-Induced Hyperhydration*", there is some evidence that glycerol hyperhydration can be maintained for up to 40 hours with ongoing ingestion of glycerol.

In "*Hyperhydration with glycerol solutions*", authored by Riedesel et al, American Physiological Society, 1987, glycerol was studied and its affect on dilute saline solution retention as well as general fluid retention.

In "*Effects of glycerol-induced hyperhydration prior to exercise in the heat on sweating and core temperature*", authored by Lyons et al, Medicine and Science in Sports and Exercise, 1990, the effects of glycerol induced hyperhydration prior to exercise in the heat or sweating and core temperature was studied. Here, exercise was started 2.5 hours after the fluids were ingested. The study concluded that glycerol induced hyperhydration reduced the thermal burden of moderate exercise.

In addition, U.S. Pat. No. 5,147,650, issued on Sep. 15, 1992, found that glycerol containing solution, compared to water or Gatorade® type drink, ingested during exercise resulted in an expanded blood volume, lower heart rate, and lower rectal temperature during exercise.

The invention herein described is a novel exercise regimen for enhancing endurance and performance in activities such as hiking, soccer, football, etc. The subject exhibits an increased total body water level and therefore an improved cardiac stroke volume in the absence of fluids or even with the use of glycerol or water in a non-regimented fashion.

BRIEF SUMMARY OF THE INVENTION

The invention relates to a novel exercise regimen for ameliorating the adverse physiological effects which result from physical exertion and heat exposure. The subject hydration regimen comprises the steps of: ingesting a solution of glycerol and water prior to inception of the exercise. The subject begins ingestion of the solution, at a given rate by mouth, two hours before the inception of the exercise and stops ½ hour prior to inception. The subject the begins to exercise and ingests a second solution comprising glycerol, carbohydrate, sodium and water at a given rate during exercise.

Combination of a pre-exercise glycerol solution hydration regimen with a glycerol/carbohydrate/sodium solution hydration regimen during exercise results in an unique and optimal methodology for improving endurance performance.

DETAILED DESCRIPTION OF THE INVENTION

The invention described herein is a novel exercise hydration regimen which has been shown to improve physiological response in subjects. Specifically, the invention comprises an exercise hydration regimen wherein a solution of from 0.78–2.0 gms/kg of glycerol and 26 ml/kg of water are ingested by mouth starting 2 hours before and continuing up until ½ hour before the start of exercise. This would correspond to a 3–8% solution of glycerol, and preferably a 4.6% solution. Total volume ingested over the 1 ½ hour hydration period is 26 ml/kg. This pre-exercise hydration regimen is then supplemented by fluid replacement during exercise. A second solution is ingested during exercise to prolong the benefit of the pre-exercise hydration. The second solution comprises from 0.4 to 1.5% glycerol, from 6–8% of a carbohydrate such as glucose and from 0–10 mEq sodium, ingested at a rate of 800–1600 ml/hr.

Glycerol hyperhydration can be maintained for up to forty hours with ongoing ingestion of glycerol. A glycerol containing solution, compared to water or glucose, results in expended blood volume, lower heart rate, and lower rectal temperature. These beneficial physiological effects improve performance.

However, gastric emptying rates are impaired by high osmolality. For example, ½ of a 5% solution of carbohydrate (250 mosm) would be emptied in 20 minutes while ½ of 12.5% solution (675 mosm) would be emptied in 45 minutes. Thus solutions containing greater than 1.5% glycerol in addition to 6% glucose significantly impair gastric emptying. A solution containing from 0.4 to 1.5% glycerol, in addition to 6–8% carbohydrate (glucose) and 0–10 mEq sodium, ingested at a rate of 800–1600 ml/hr enhance hydration during exercise and prolong performance.

The combination of pre-exercise glycerol enhanced hydration regimen and glycerol enhanced hydration regimen during exercise produces a unique and optimal exercise regimen to enhance endurance and performance.

What is claimed is:

1. A pre-exercise glycerol enhanced hyper hydration formulation comprising a carbohydrate free solution of water and glycerol, wherein said sole active ingredient consists of glycerol present in a proportion of from 3% to 8% of said solution.

2. A pre-exercise glycerol enhanced hyper hydration formulation in accordance with claim 1, wherein said solution is 4.6% glycerol.

3. An exercise supplemented glycerol enhanced hyper hydration formulation comprising water, 0.4% to 1.5% glycerol, 6% to 8% carbohydrate and up to 10 mEq sodium.

* * * * *